(12) United States Patent
Pennie

(10) Patent No.: US 11,576,658 B2
(45) Date of Patent: Feb. 14, 2023

(54) BONE MARROW ASPIRATE COLLECTION SYSTEM

(71) Applicant: Patrick Pennie, Fort Myers, FL (US)

(72) Inventor: Patrick Pennie, Fort Myers, FL (US)

( * ) Notice: Subject to any disclaimer, the term of this patent is extended or adjusted under 35 U.S.C. 154(b) by 310 days.

(21) Appl. No.: 16/799,301

(22) Filed: Feb. 24, 2020

(65) Prior Publication Data

US 2020/0268360 A1    Aug. 27, 2020

Related U.S. Application Data

(60) Provisional application No. 62/809,342, filed on Feb. 22, 2019.

(51) Int. Cl.
*A61B 10/02* (2006.01)
*A61B 17/34* (2006.01)

(52) U.S. Cl.
CPC ........ *A61B 10/025* (2013.01); *A61B 17/3472* (2013.01); *A61B 17/3421* (2013.01); *A61B 2010/0258* (2013.01); *A61B 2017/3456* (2013.01)

(58) Field of Classification Search
CPC .................................................. A61B 10/025
See application file for complete search history.

(56) References Cited

U.S. PATENT DOCUMENTS

2014/0257133 A1* 9/2014 Landrigan ............ A61B 10/025
600/566

* cited by examiner

*Primary Examiner* — Christian A Sevilla
(74) *Attorney, Agent, or Firm* — William E. Noonan

(57) ABSTRACT

A system and method for collecting bone marrow includes a trocar component having an upper handle and an elongate shaft depending from the handle, the shaft having a sharp cutting edge at a lower tip thereof. An introducer component includes a lower handle having an inlet formed therethrough and an introducer cannula communicably connected to the inlet and depending from the lower handle. The introducer cannula has an open distal end. The harvesting component includes a support hub having an aspiration port and a harvesting cannula communicably connected to the aspiration port and depending from the support hub. The trocar and introducer components are introduced into the bone marrow and the trocar component is replaced by the harvesting component. The introducer cannula is withdrawn and interengaged with the support hub of the harvesting component and the assembly is manipulated to drive a blunt end of the harvesting component through the bone marrow without causing undue damage to the bone marrow and constituent cells. Bone marrow is aspirated through fenestrated openings in the side wall of the harvesting cannula.

19 Claims, 8 Drawing Sheets

BONE MARROW ASPIRATE COLLECTION SYSTEM

RELATED APPLICATION

This application claims the benefit of Provisional Application Ser. No. 62/809,342 filed Feb. 22, 2019.

FIELD OF THE INVENTION

This invention relates to a bone marrow aspirate collection system and, more particularly, to a system for harvesting bone marrow aspirate that yields an improved high quality concentration of regenerative progenitor stem cells for use in medical applications.

BACKGROUND OF THE INVENTION

Progenitor stem cells are conventionally used to promote bone and tissue healing and in other medical therapies and treatments. Such stem cells are commonly derived from bone marrow aspirate, which is obtained using various available surgical instruments. Typically, a sharp tipped trocar is used to pierce and penetrate the trabecular or "spongy" bone of the patient. Liquid bone marrow is then aspirated through the trocar or other sharp edged cannula and further processed to obtain the needed stem cells.

Conventional bone marrow aspirating tools tend to produce aspirate samples having a less than optimal sample quality and stem cell concentration. Grinding the sharp cutting edge employed by the trocar through the bone marrow can cause considerable cell damage and resultant sample degradation. Many of the impacted red blood cells contained in the bone marrow undergo hemolysis and are ruptured or destroyed. This, in turn, causes the attached red blood cells to release free hemoglobin molecules, which are oxidative and very destructive of tissue. The disruption of the bone marrow that accompanies the use of conventional trocars also produces clotting and tissue activation, which can significantly reduce the therapeutic effectiveness of the aspirate sample. Traditional open tip aspirating cannulas having a sharp or thin bottom edge can cause similar adverse effects when penetrating the trabecular bone to collect bone marrow aspirate.

SUMMARY OF THE INVENTION

This invention results from a realization that a significantly improved, high quality bone marrow aspirate may be more effectively collected by aspirating the bone marrow sample through a blunt-tipped harvesting cannula that is introduced to a desired collection site within the bone marrow without unduly damaging the red blood cells and degrading the aspirate sample as has previously occurred when conventional sharp edge trocars and open tip cannulas are used for bone marrow aspiration.

It is therefore an object of the present invention to provide a bone marrow aspirate collection system that successfully harvests an improved high quality bone marrow aspirate sample without causing excessive damage to the sample and red blood cells contained therein.

It is a further object of this invention to provide a bone marrow aspirate collection system that enables an increased concentration of high quality progenitor stem cells to be retrieved from an aspirate sample.

It is a further object of this invention to provide a bone marrow aspirate collection system that significantly reduces tissue activation, free hemoglobin content, oxidation, blood clotting and other problems that degrade harvested aspirate samples when conventional bone marrow aspirating instruments are used.

It is a further object of this invention to provide a bone marrow aspirate collection system that yields an aspirate sample that may be effectively processed to obtain a product that is supraphysiologic in regenerative progenitor stem cells.

It is a further object of this invention to provide a bone marrow aspirate collection system that more effectively produces high quality and more concentrated progenitor stem cells for use in medical therapies and treatments.

It is a further object of this invention to provide a bone marrow aspirating system employing a blunt tip harvesting cannula with a plurality of relatively large aspiration holes formed in a side wall of the cannula, which may be advanced smoothly to a selected location in the bone marrow and without advancing an accompanying trocar or open tip introducer through the marrow, and which therefore significantly reduces resulting damage to the bone marrow and constituent red blood cells to yield a significantly improved aspirate sample.

This invention features a bone marrow aspirate collection system including a trocar component having an upper handle at an upper end thereof and an elongate shaft that is connected to the handle and depends therefrom to terminate in a cutting edge at a lower end or tip of the shaft. An introducer component includes a lower handle and an introducer cannula that is connected to and depends from the lower handle. An introducer inlet is formed through the lower handle in communication with the introducer cannula. The trocar shaft is insertible longitudinally through the inlet of the introducer component and through the introducer cannula such that when the upper handle of the trocar component and the lower handle of the introducer component are interengaged, the cutting edge tip of the trocar shaft is disposed beyond an open lower end of the introducer cannula. A harvesting component includes a support hub that carries an elongate harvesting cannula depending from the support hub. An aspiration port is communicably connected through the support hub to an upper end of the harvesting cannula. An opposite lower end of the harvesting cannula includes a blunt tip. The harvesting cannula is fenestrated and includes one or more aspiration openings formed above and proximate to the blunt tip along a longitudinal side of the harvesting cannula. The upper and lower handles of the trocar and introducer components, respectively, are selectively disengaged and separated to withdraw the trocar shaft from the introducer cannula. This releases the trocar component from the introducer component. The harvesting component is then selectively interengaged with the introducer component by inserting the harvesting cannula through the introducer inlet and cannula such that the blunt tip of the harvesting cannula is disposed beyond the open lower end of the introducing cannula and the support hub of the harvesting cannula releasably engages the lower handle of the introducer cannula.

In a preferred embodiment, the trocar component includes a connector section that is carried by the upper handle. The connector section and the inlet of the introducer component may include respective elements that are releasably interengaged to lock the trocar and the introducer components together. The support hub of the harvesting component and the introducer inlet may also have complementary elements for releasably interlocking the harvesting and introducer components together when those components are interengaged.

The introducer cannula and harvesting cannula may include respective depth guidelines or markings formed at selected intervals along each cannula, which indicate the depth that each cannula is inserted at the surgical site.

The aspiration port of the harvesting component may include threads or other means for releasably and operably interconnecting an aspirating syringe to the harvesting component. The support hub may itself support a mallet cap that is releasably attached to a top of the support hub by corresponding threads or other means. This mallet cap may be utilized to facilitate movement of the harvesting cannula through the bone marrow.

The invention also relates to a method of employing the system to collect bone marrow aspirate. A trocar component, introducer component and harvesting component are provided as previously described. The elongate shaft of the trocar component is aligned with and inserted through the introducer inlet and introducer cannula such that the sharpened tip of the trocar shaft extends beyond the lower open end or tip of the introducer cannula. The upper and lower handles are interengaged and the assembled trocar and introducer components are manipulated to insert the introducer cannula and accommodated trocar shaft through the skin, underlying tissue and cortical bone of the patient until the cutting edge tip of the trocar shaft penetrates a short distance into the bone marrow. This step is performed by grasping the interengaged upper and lower handles and engaging the exposed, sharp cutting edge tip of the trocar component against the patient. The handles are pushed such that the interengaged introducer cannula and trocar shaft are driven through the patient to the trabecular bone containing the bone marrow. Specifically, the sharp cutting edge pierces the patient's skin, underlying tissue and outer cortical bone. The trocar is introduced a short distance, typically not more than about 1 cm, into the spongy bone containing the bone marrow. The open lower end of the introducer cannula is also preferably positioned slightly within or just outside of the bone marrow.

After the assembled introducer cannula and trocar shaft are successfully positioned in the foregoing manner, the upper and lower handles are disengaged from one another. The user grasps the upper handle and pulls/retracts the trocar component outwardly to remove the trocar shaft from the introducer cannula and thereby from the patient. The introducer component remains within the patient, with the lower end of the introducer cannula preferably held slightly within or just outside of the spongy bone or bone marrow region.

The aspirate harvesting component is then interengaged with the introducer component by inserting the elongate harvesting cannula into the inlet of the introducer component. The harvesting cannula is slid longitudinally through the introducer cannula until the blunt tip of the harvesting cannula is positioned beyond the open lower end of the introducer cannula within the trabecular bone region of the patient. The user then grasps the lower handle of the introducer component and withdraws the introducer cannula along the harvesting cannula until the inlet port of the introducer component engages the support hub of the harvesting component. At this point, the introducer cannula is typically withdrawn completely from the patient. The user may then grasp the support hub of the harvesting component and the interengaged lower handle of the introducer component and manipulate the assembled introducer and harvesting components to position the fenestrated end portion of the harvesting cannula at a selected depth and location within the trabecular bone region. Specifically, the interengaged support hub and lower handle are pushed to drive the blunt tip of the harvesting cannula to the selected depth/location within the spongy bone region. The optional mallet cap may be attached to the support hub of the harvesting component, threadably or otherwise, to assist insertion of the harvesting cannula through the bone marrow. The blunt tip and positioning of the fenestrated aspiration openings along the longitudinal sides of the harvesting cannula significantly reduce disruption of the bone marrow and damage to the red blood cells during positioning of the harvesting component within the bone marrow.

After the harvesting cannula is successfully positioned within the bone marrow at a selected depth and location, an aspirating syringe is operably interconnected to the aspirating port of the harvesting component. If a mallet cap is attached, that cap is removed from the support hub of the harvesting component. The syringe is then operated to gently draw aspirate from the bone marrow and into the harvesting cannula through the fenestrated openings. As bone marrow is aspirated, the assembled introducer and harvesting components are slowly withdrawn to remove the introducer cannula from the trabecular bone. The aspirated bone marrow is then processed to yield a significantly improved, relatively undamaged product containing a high concentration of progenitor stem cells, which can be used effectively in various medical therapies, treatments and procedures.

Preferably, the trocar and introducer components are releasably interlocked during introduction of the introducer cannula and trocar shaft into the trabecular bone. After that step is completed, the trocar component is unlocked from the introducer component and the trocar shaft is withdrawn from the introducer cannula. By the same token, the support hub of the harvesting component may be releasably interlocked with the lower handle of the introducer component prior to manipulating the assembled introducer component and harvesting component to position the harvesting cannula at a selected depth and location within the bone marrow. After aspiration is completed the assembled introducer and harvesting components may be withdrawn from the patient and unlocked and disengaged from one another.

BRIEF DESCRIPTION OF THE DRAWINGS

Other objects, features and advantages will occur from the following description of a preferred embodiment and the accompanying drawings, in which.

DETAILED DESCRIPTION OF PREFERRED EMBODIMENTS

Figure 1:
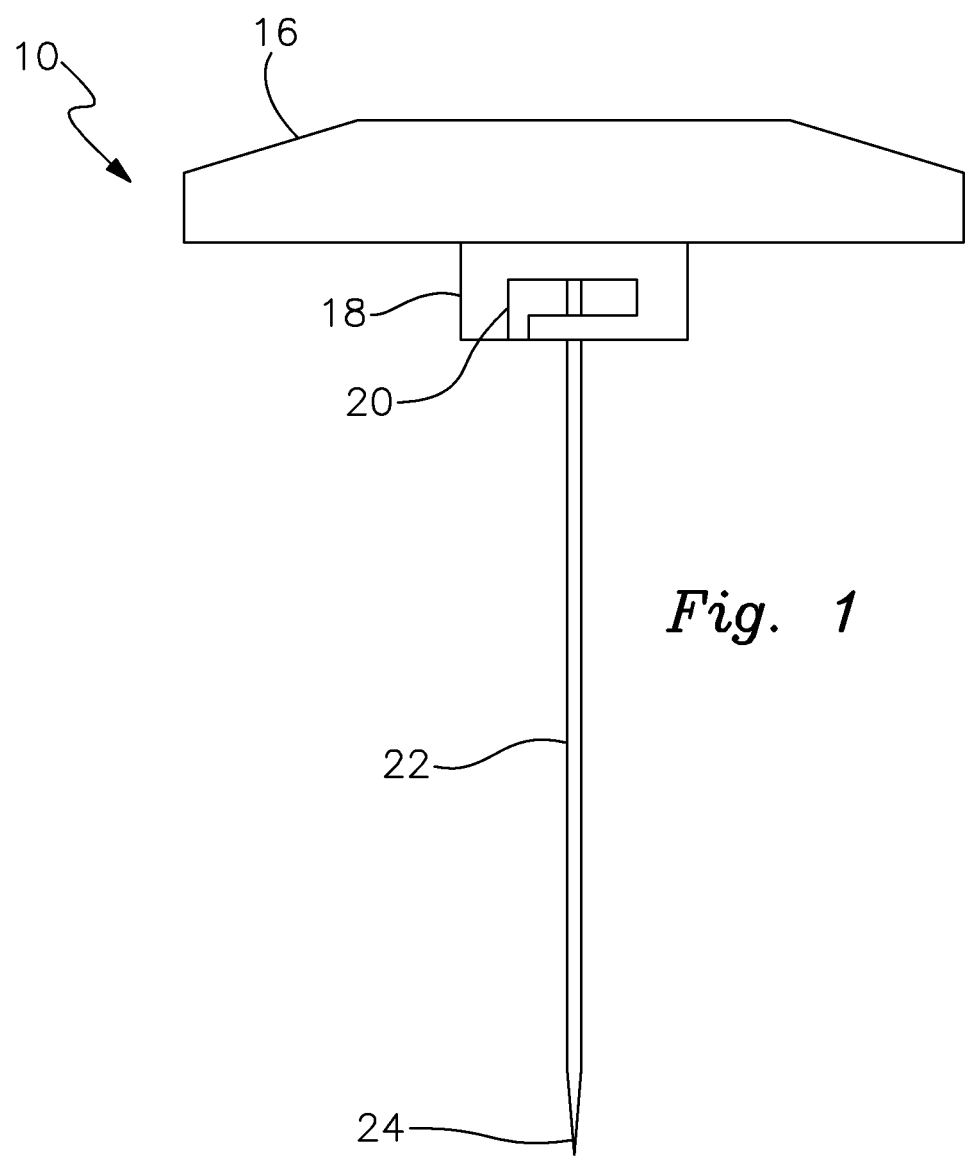
FIG. 1 is an elevational front view of the trocar component.
Figure 2:
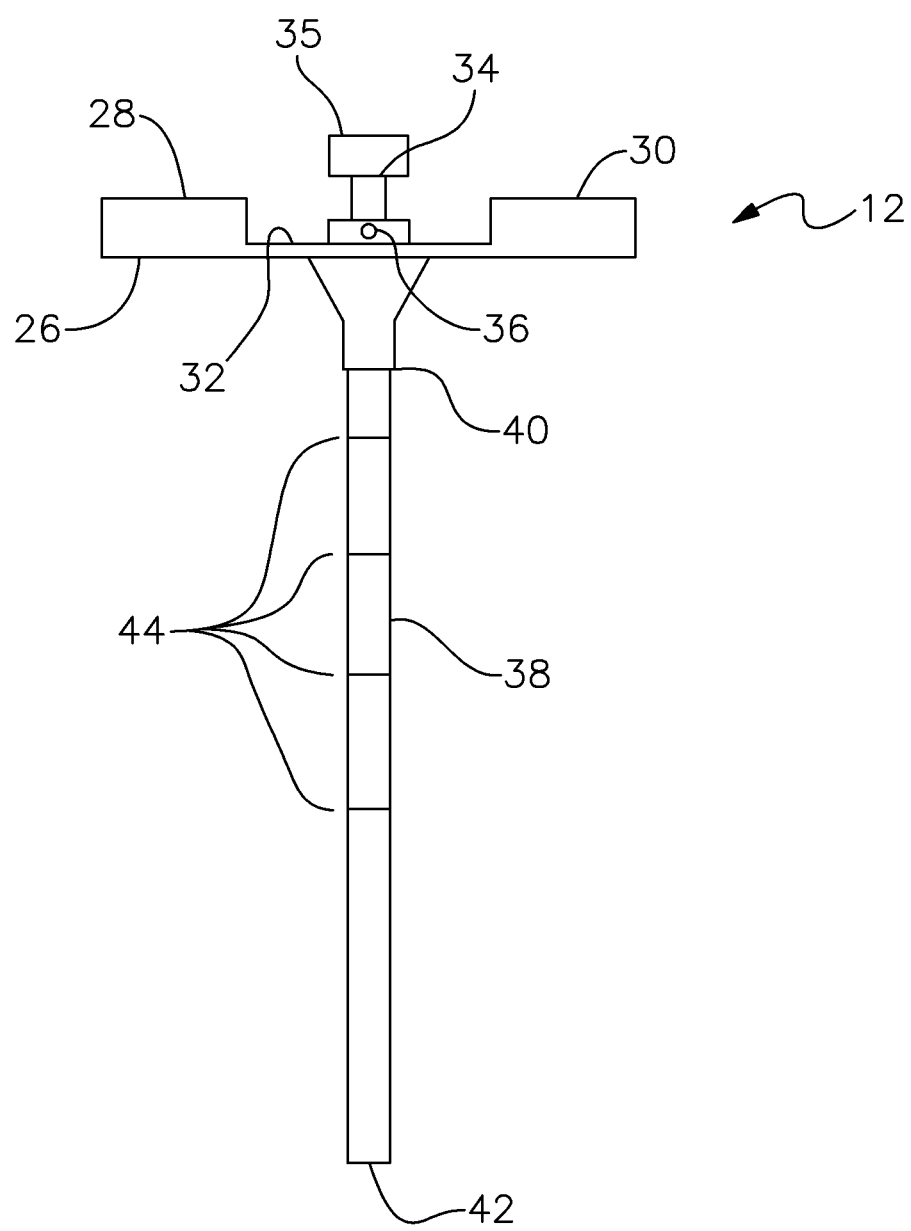
FIG. 2 is an elevational front view of the introducer component.
Figure 3:
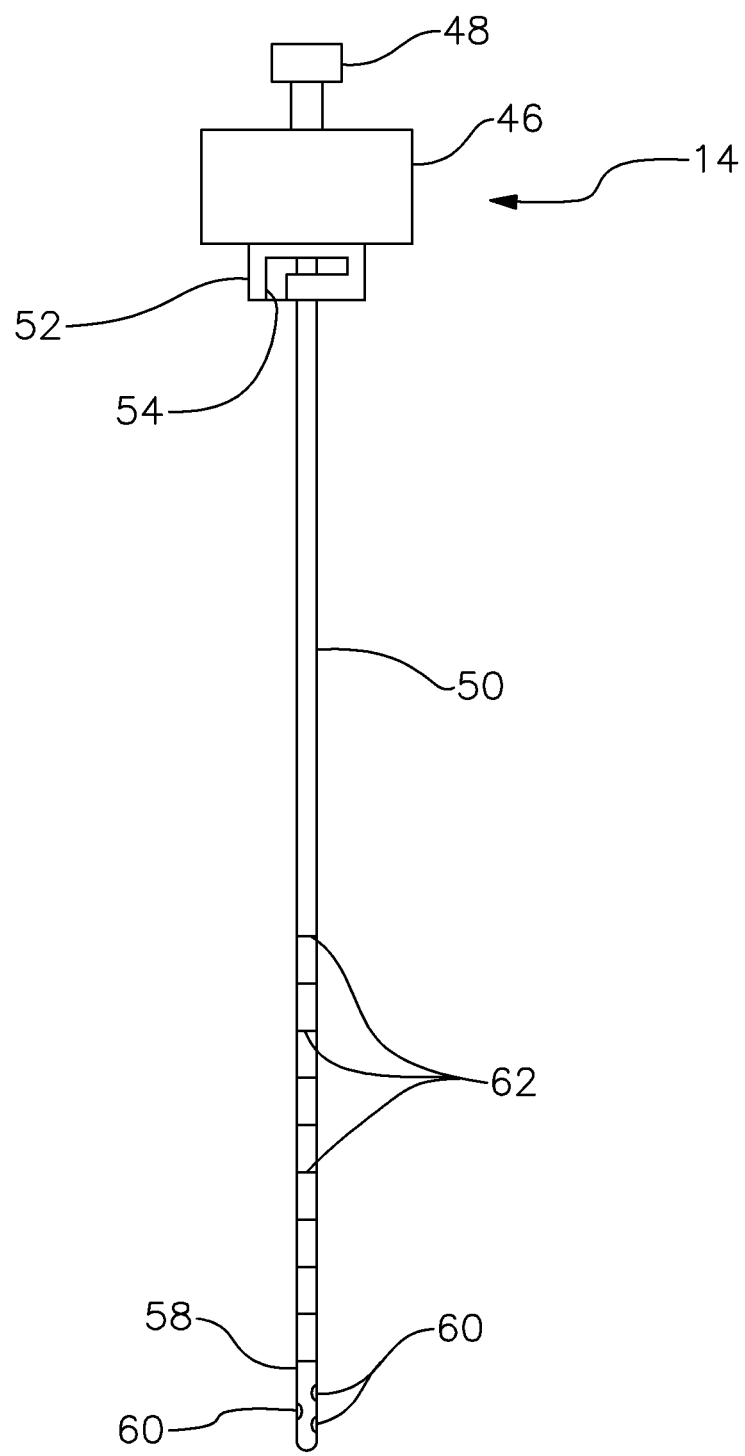
FIG. 3 is a front elevational view of the harvester component.

The system and method of this invention employ three separate pieces, namely a trocar component 10 shown alone in FIG. 1, an introducer component 12, shown alone in FIG. 2 and a harvester component 14, shown alone in FIG. 3. These components are sequentially assembled, operated and disassembled to perform bone marrow aspiration in the manner described below.

As shown in FIG. 1, trocar component 10 includes an upper handle 16 featuring an ergonomic shape that makes the upper handle easy to grasp and manipulate when collecting a bone marrow aspirate sample. Handle 16 is typically composed of a medical grade plastic or other material suitable for medical and surgical uses. A generally annular connector section 18 is carried by and depends from the bottom of upper handle 16. A generally L-shaped locking slot 20 is formed in annular connector section 18. The locking slot operates to interlock trocar component 10 to introducer component 12 when those components are assembled for use in the manner described below.

An elongate needle, stylet or trocar shaft 22 depends centrally from the bottom of handle 16. In particular, shaft 22 extends through and below annular connector section 18. The lower end or tip of trocar shaft 22 has an extremely sharp cutting edge 24. This may comprise a razor sharp triple crown bevel tip that is known to be effective for performing minimally invasive coring of the cortical bone surrounding the spongy bone marrow. Shaft 22 and cutting edge tip 24 are typically composed of a surgical grade metal or metal alloy material.

Introducer component 12, FIG. 2, includes a lower handle 26 featuring an opposing pair of arms 28 and 30 interconnected by a narrower recessed portion 32. Once again, lower handle 26 is preferably composed of a medical or surgical grade plastic. An introducer cannula inlet 34 is formed through recessed portion 32 of lower handle 26. Inlet 34 includes an interior bore or passageway extending between open top and bottom ends 35 and 40, respectively. Typically, cannula inlet 34 is molded or otherwise formed unitarily with handle 26, although in alternative versions, the handle and cannula inlet may comprise distinct interconnected pieces. Inlet 24 carries a locking pin 36 that extends radially outwardly from the cannula inlet within the recessed region of the handle. Locking pin 36 cooperates with previously specified locking slot 20 releasably to secure trocar component 10 to introducer component 12 during use of the system in the bone marrow aspiration process.

An elongate introducer cannula 38 is communicably connected to open lower end 40 of cannula inlet 34. Cannula 38 has a tubular or cylindrical cross sectional shape and is again typically composed of a surgical grade metal or metal alloy. The introducer cannula has an inner bore diameter that is larger than the diameter of trocar shaft 22. Cannula 38 features a length that is shorter than the length of trocar shaft 22 such that the trocar shaft extends beyond the open lower end 42 of introducer cannula 38 when components 10 and 12 are interengaged, as described more fully below. A circular, open lower end 42 is formed in cannula 38 for accommodating and transmitting the distal tips of the trocar shaft 22 and the harvesting cannula of component 14 in a manner that is described more fully below.

A plurality of graduated depth marking rings 44 are formed annularly about the outside surface of cannula 38 at selected distances to mark corresponding depths or distances along the cannula. For example, in the version shown in FIG. 2, marking rings 44 may be formed at depths of 20, 30, 40 and 50 mm from bottom to top, which designate respective depths to which the introducer cannula may be introduced into the patient. The number of graduated markings 44 and the corresponding depths designated thereby may be varied within the scope of this invention.

FIG. 3 depicts harvesting component 14 that is selectively and sequentially interengaged with introducer component 12 during use and operation of the aspirating system. Harvester component 14 includes a generally cylindrical cannula support hub 46 that is composed of similar materials to those comprising the upper and lower handles of the trocar and introducer components respectively. Support hub 46 supports an aspirating port 48 that extends upwardly from the support hub. An elongate harvesting cannula 50 is likewise supported by support hub 46 and depends therefrom. Cannula 50 is communicably interconnected to aspirating port 48 within hub 46. The support hub may have various shapes and configurations and the upper end of cannula 50 may be communicably secured to the lower open end of port 48 in various manners within the scope of this invention. Cannula 50 may be formed of a medical or surgical grade metal similar that comprising the trocar shaft and introducer cannula.

Support hub 46 also carries an annular harvesting connector section 52 having an L-shaped locking slot 54. Connector section 52 and slot 54 are analogous to the connector section 18 and locking slot 20 employed by trocar component 10. This structure enables the harvesting component 14 to be lockably interconnected with the introducer component 12 when those parts are assembled for use in connection with the system as described below. It should also be noted that the harvesting component 14 may employ different structure, within the scope of this invention, for supporting the harvesting cannula, for example, as is shown and described below in connection with FIGS. 8 and 9.

Harvesting cannula 50 features a metal or metal alloy construction analogous to that employed for the trocar shaft 22 and introducer cannula 38. Cannula 50 has an outer diameter that allows the harvesting cannula to fit slidably though the interior bore of introducer cannula 58. The length of cannula 50 is significantly longer than that of either trocar shaft 22 or introducer cannula 38. As a critical feature of this invention, cannula 50 is provided with a blunt, smoothly rounded distal tip 56. As used herein, "blunt" should b understood to include and refer to an unperforated, smoothly rounded or exteriorly convex tip. This blunt tip is fully closed and not open in the manner of the distal open end tip 42 of introducer cannula 38. Cannula 50 also includes a fenestrated side wall 58 including three relatively large diameter aspiration holes 60 formed in the side wall 58 of cannula 50 above and proximate to the blunt lower tip 56 of the harvesting cannula. As shown in FIGS. 3, 5, 6 and 7 two of the aspiration holes 60 are generally aligned on one longitudinal side of the cannula and the third hole is located in a generally diametrically opposed location on cannula 50. Typically the third aspiration hole is larger than either of the aligned pair of holes on the opposite side, although the hole sizes and number of holes may be varied within the scope of this invention. A plurality of graduated depth markings or rings 62 are formed at preselected distances along harvesting cannula 50. Respective depths may be printed on cannulas 38 and/or 50, as desired.

The trocar, introducer and harvesting components 10, 12 and 14 respectively, are assembled and utilized to collect a much purer quality bone marrow sample that can be processed to obtain a significantly higher concentration of progenitor stem cells for beneficial use in medial therapies and treatments. That process is performed as follows.

Figure 4:
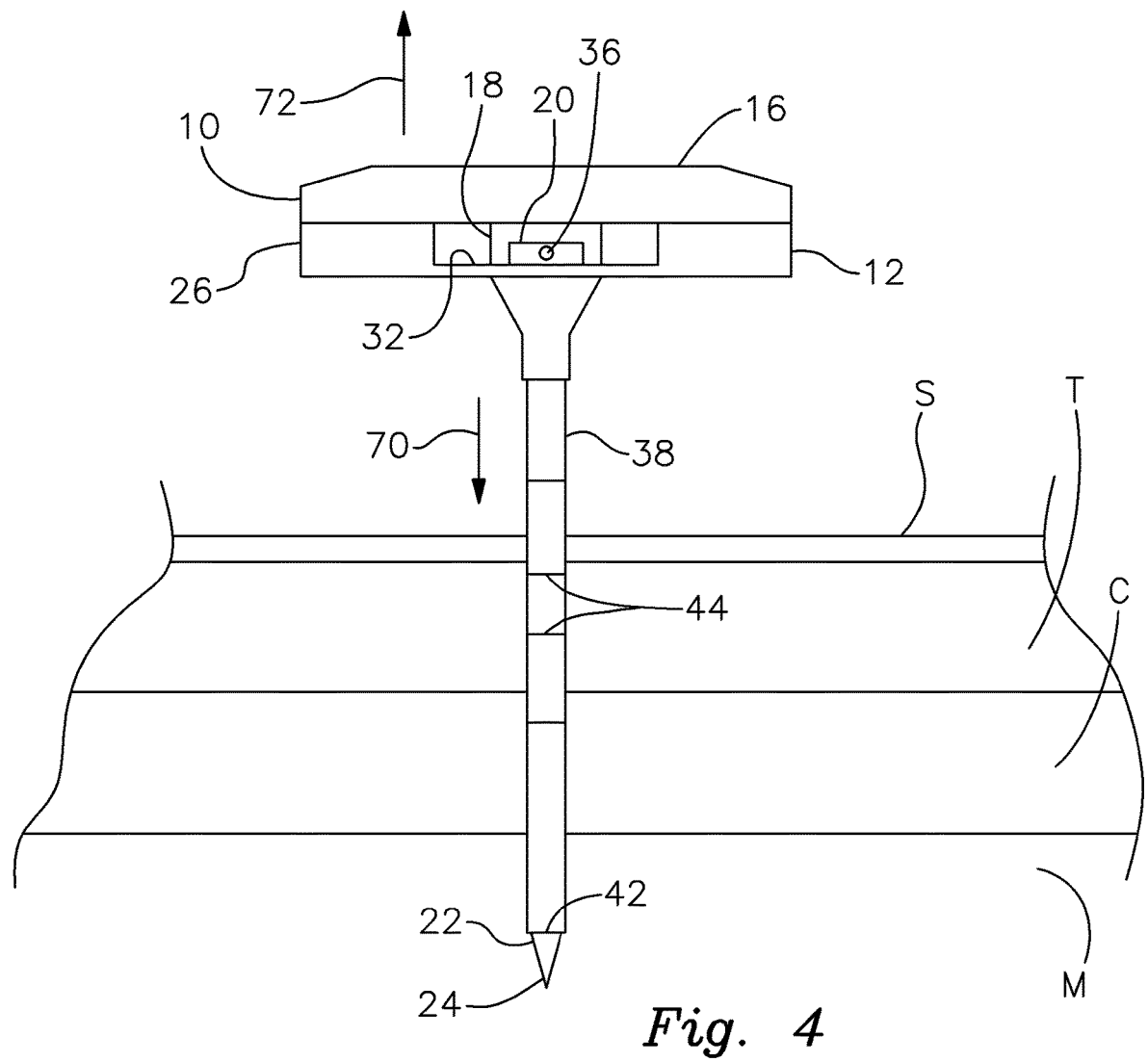
FIG. 4 is an elevational, partly cross sectional front view of the assembled trocar and introducer components inserted into a patient's bone marrow.

As shown in FIG. 4, trocar component 10 and introducer component 12 are initially assembled. More particularly, trocar shaft 22 (FIG. 1) is aligned with open upper end 35 of introducer inlet 34 (FIG. 2). The trocar shaft is then slid longitudinally through the central opening of inlet 34 and through the central passageway or bore of communicably interconnected introducer cannula 38. The trocar shaft is driven through the introducer cannula until upper handle 16 of trocar component 10 engages lower handle 26 of introducer component 12. See FIG. 4. As a result, cutting edge tip 24 of trocar shaft 22 extends slightly (e.g. approximately 1 cm) beyond the open lower end 42 of introducer cannula 38. Annular connector section 18 is received within the recess 22 of lower handle 26. Trocar handle 16 is rotated in a first direction relative to introducer handle 26 and pushed against handle 26 such that L-shaped slot 20 of trocar component 10 receives locking pin 36 of introducer component 12. The trocar upper handle 16 is turned to lockably interengage pin 36 and slot 20 as shown in FIG. 4. This aligns handles 16 and 26 and locks the trocar component 10 onto the introducer component 12.

The assembled and interlocked trocar component 10 and introducer component 12 are next introduced into the bone marrow of a patient as further shown in FIG. 4. In particular, the surgeon, physician or other medical personnel directs the exposed cutting edge tip 24 of trocar shaft 22 to pierce the skin S and underlying fat/tissue T, as well as the and cortical bone C of the patient. Pressure is applied on the interengaged handles 12 and 16 (typically using an alternating clockwise/counterclockwise motion) such that the extremely sharp triple crown cutting edge tip 24 passes smoothly through skin S and fat/tissue T and grinds through cortical bone C in a minimally invasive manner. The lower end of the introducer cannula 38 and the exposed trocar cutting edge 24 are introduced only a very short distance (typically not greater than 1 cm) into the spongy bone marrow layer M. Little or no damage is thereby caused to the marrow and its constituent red blood cells.

After the trocar and introducer components have been properly positioned in the foregoing manner, trocar component 10 is released from introducer component 12 and withdrawn from the patient. Specifically, upper handle 16 is rotated in an opposite second direction relative to lower handle 26 until locking pin 36 is aligned with the vertical leg of locking slot 20. The trocar handle is then disengaged from introducer handle 26 in the direction of arrow 72, FIG. 4, and trocar shaft 22 is withdrawn from introducer cannula 38 and cannula inlet 34 (FIG. 2).

Figure 5:
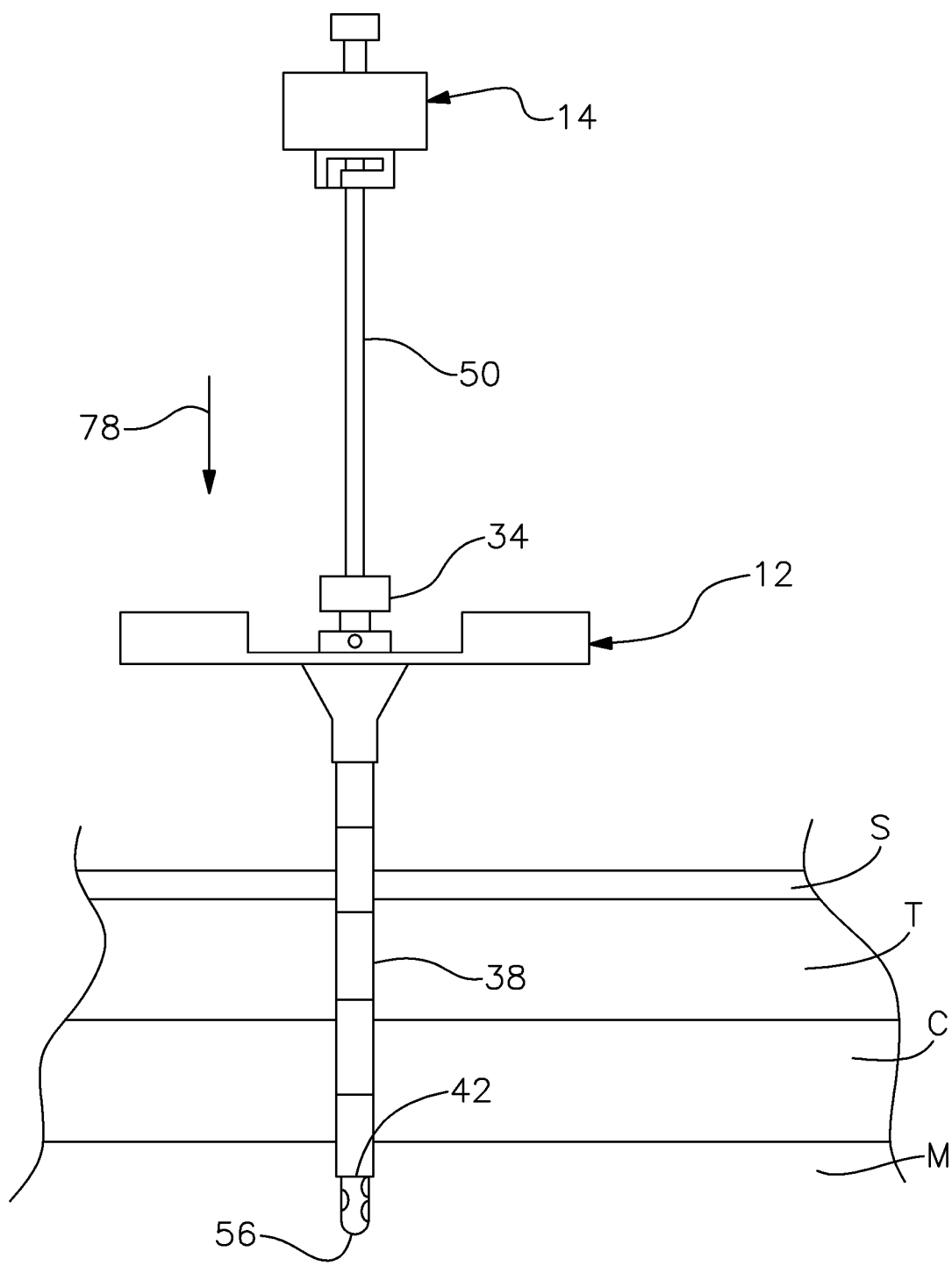
FIG. 5 is an elevational, partly cross sectional front view depicting the assembled harvesting and introducer components with the blunt tip of the harvesting cannula initially inserted a slight distance into the bone marrow.

Next, trocar component 10 is replaced by harvesting component 14 as shown in FIG. 5. Harvesting component 14 is positioned such that harvesting cannula 50 is aligned with open top end 35 of inlet 34 and communicably attached introducer cannula 38 of introducer component 12. Harvesting component 14 is then manipulated as shown in FIG. 5 to insert harvesting cannula 50 longitudinally through inlet 34 and communicably attached cannula 38. The harvesting cannula 50 is transmitted through introducer cannula 38 in this manner until the lower blunt tip 56 of harvesting cannula 50 extends beyond the lower open end 42 of introducer cannula 38. The lower or distal blunt tip of harvesting cannula 50 thereby effectively assumes the position where the withdrawn sharp cutting edge tip of the trocar component was situated, i.e. the blunt tip of harvesting cannula 50 is now positioned at a depth of about 1 cm or less within bone marrow M.

Figure 6:
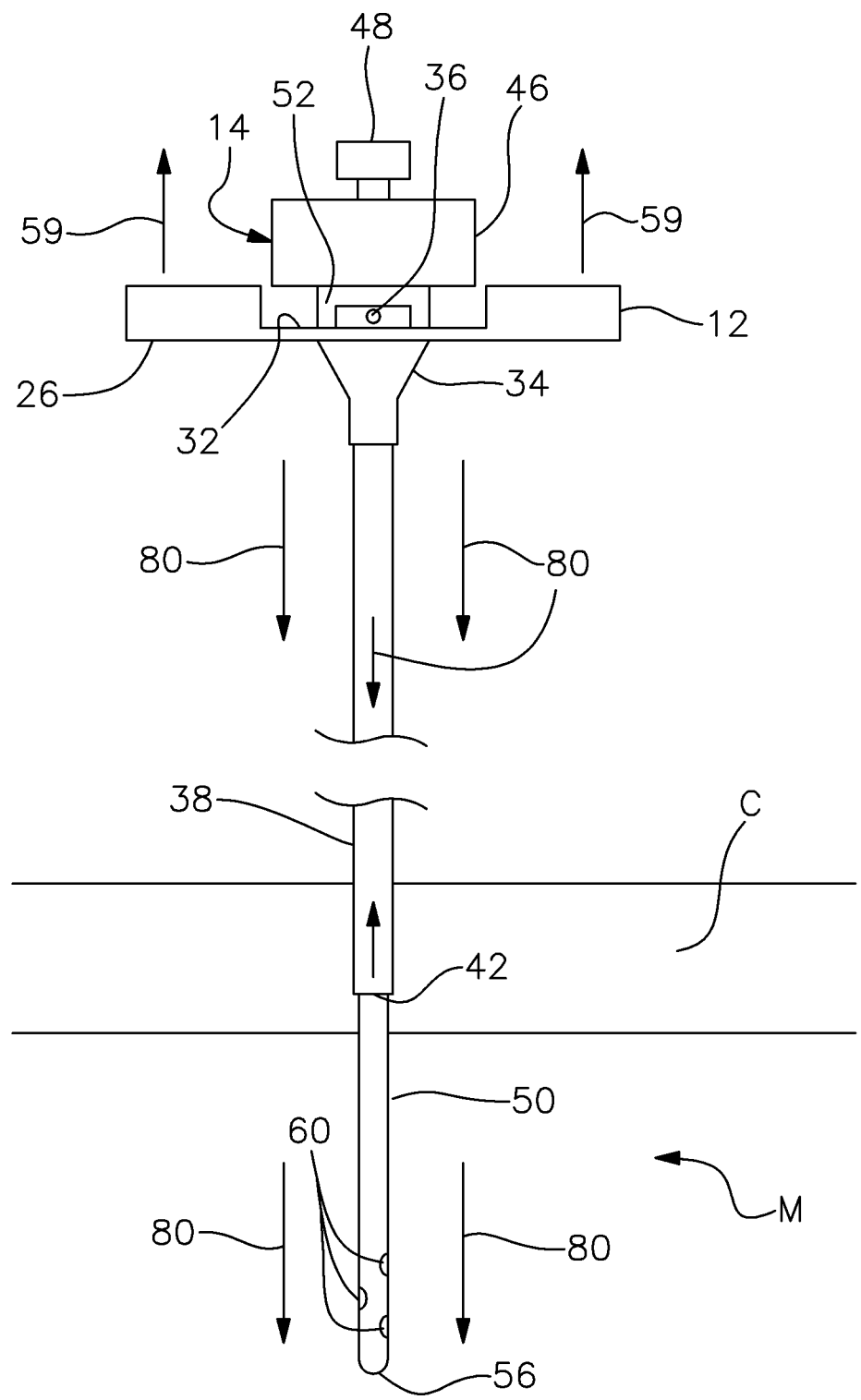
FIG. 6 is an elevational, partly cross sectional and fragmentary view of the introducer component in a retracted position relative to the interengaged harvesting component and further depicting the assembled components being manipulated to position the harvesting component at a selected depth and location within the bone marrow.

After the interengaged introducer and harvesting components have been positioned in the foregoing manner, introducer component 12 is retracted from the patient in the manner shown in by arrows 59 FIG. 6. Specifically, the user grasps handle 12 and retracts introducer cannula 38 upwardly along harvesting cannula 50. The introducer cannula may be withdrawn until the lower end 42 of cannula 38 is completely removed from the patient. Using this technique, the lower end of the introducer cannula 38 should be fully withdrawn from the bone marrow M and preferably from the cortical bone as well. Handle 26 is retracted until it engages support hub 46 and/or connector section 52 of harvesting component 14. Locking pin 36 carried by introducer inlet 34 is properly positioned by turning lower handle 26 until the locking pin is aligned with the vertical section of the locking slot 54 (FIG. 3) carried by support hub 46 of harvesting component 14. The locking pin 36 and corresponding locking slot 54 are interengaged and handle 26 is turned to interlock the introducer and harvesting components 12 and 14 respectively. Again, at this point, the lower end 42 of introducer cannula 38 is fully withdrawn from bone marrow M and also may be fully removed from the patient's incision. The lower end 56 of harvesting cannula 50 remains positioned at a depth of approximately 1 cm or less within the bone marrow.

The interlocked introducer component 12 and harvesting component 14 are then driven downwardly in the manner indicated by arrows 80 in FIG. 6. Harvesting cannula 50 advances through bone marrow M in a smooth relatively gentle and minimally invasive manner that does not cause undue damage to the bone marrow or its constituent cells. By properly manipulating the assembled introducer component 12 and harvesting component 14 the physician or other user can direct the blunt tip of the harvesting cannula and the aspiration holes 60 of the fenestrated longitudinal sides of that cannula to a selected location of the bone marrow wherein harvesting is to be performed. The user can quite easily turn the advancing harvesting cannula in various directions as desired and due to the smooth and rounded blunt leading cannula tip 56, the bone marrow and its cells are not seriously damaged or degraded. The harvesting cannula is not advanced beyond a point where the lower end 42 of introducer cannula 38 would re-enter bone marrow M. Preferably, cannula end 42 should remain within and not be advanced beyond fatltissue layer T. It is likewise preferred that the assembled introducer and harvesting components not be operated to advance the leading end 42 of introducer cannula 38 beyond the interface of the cortical bone and trabecular bone. The user thereby avoids reintroducing the introducer cannula into the bone marrow and its constituent cells and minimizes potential damage to the marrow that could be caused by the introducer cannula.

Using an alternative preferred technique, the harvesting cannula may first be fully inserted through the introducer cannula 38 until harvesting cannula 50 extends a greater distance (e.g. 3-5 cm) beyond leading end 42 of cannula 38 and into the bone marrow. The introducer cannula is not retracted and remains in place in the patient until support hub 46 engages and is interlocked with lower handle 26 of introducer component 12. In such cases, the leading end of the introducer cannula remains proximate or within the bone marrow cavity during the subsequent aspiration process described below. However, the leading end 42 of introducer cannula 38 is not pushed or advanced through the bone marrow as the harvesting cannula 50 is advanced through the bone marrow. As a result, undue damage to the bone marrow cells is again avoided.

Figure 7:
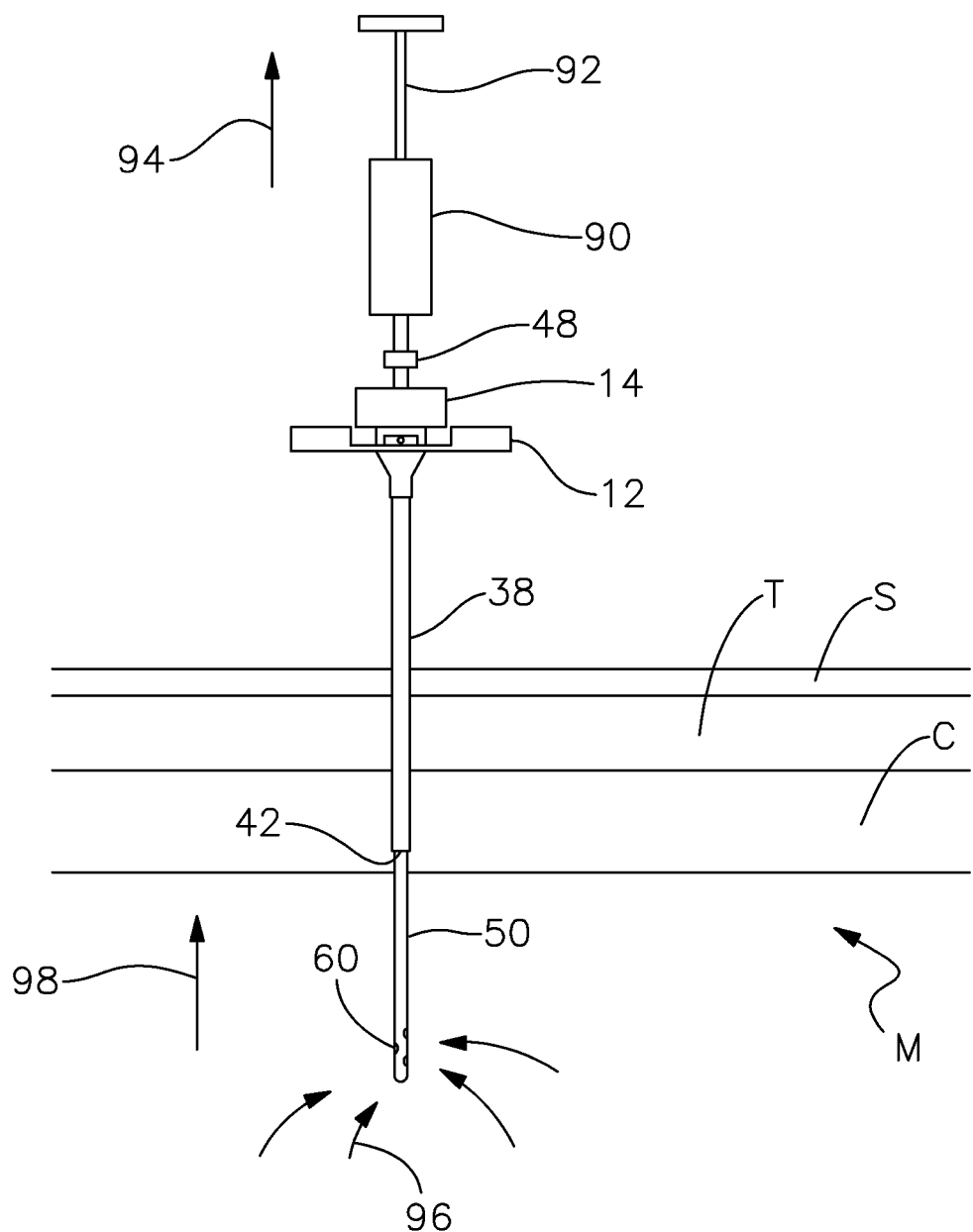
FIG. 7 is an elevational, front view of the assembled introducer and harvester components and further showing an aspirating syringe operably connected to the harvesting component and being operated to aspirate bone marrow.

When the harvesting cannula 14 has been property positioned within bone marrow M, a bone marrow sample is the aspirated as shown in FIG. 7. In particular, an aspirating syringe 90 is operably interengaged with aspirating port 48 of harvesting component 14. The aspirating port may comprise a Luer port or other type of known port for performing medical aspiration procedures. This operably interengages syringe 90 with the harvesting cannula 50 communicably connected to port 48. The user operates syringe 90 by retracting the handle 92 of syringe, as indicated by arrow 94. This causes syringe 90 to draw liquefied bone marrow into harvesting cannula 50 through aspirating holes 60 as indicated by arrows 96. This material is aspirated gradually and fairly slowly through cannula 50 and port 48, and collected within syringe 90. At the same time that aspiration is being performed, the assembled introducer and harvesting components are slowly withdrawn to remove harvesting cannula 50 from the bone marrow as indicated by arrow 98. This operation, when combined with the relatively large size of the aspiration holes 60 in the fenestrated side walls of cannula 50, creates a very gentle flow of liquefied bone marrow aspirate, which further minimizes damage to and improves the quality of the aspirated sample. In some embodiments, the assembled introducer and harvesting components may be partially and sequentially withdrawn from the bone marrow cavity in one or more successive selected increments (e.g. 1 cm each) and additional bone marrow may be aspirated at each interval. The process may be continued sequentially until aspiration is completed.

After aspiration is completed, the assembled introducer component 12 and harvesting component 14 are removed from the patient and disassembled from one another by simply turning the handle 26 of introducer component 12 to disengage the locking pin 36 from the locking slot 54 of the harvesting component.

Figure 8:
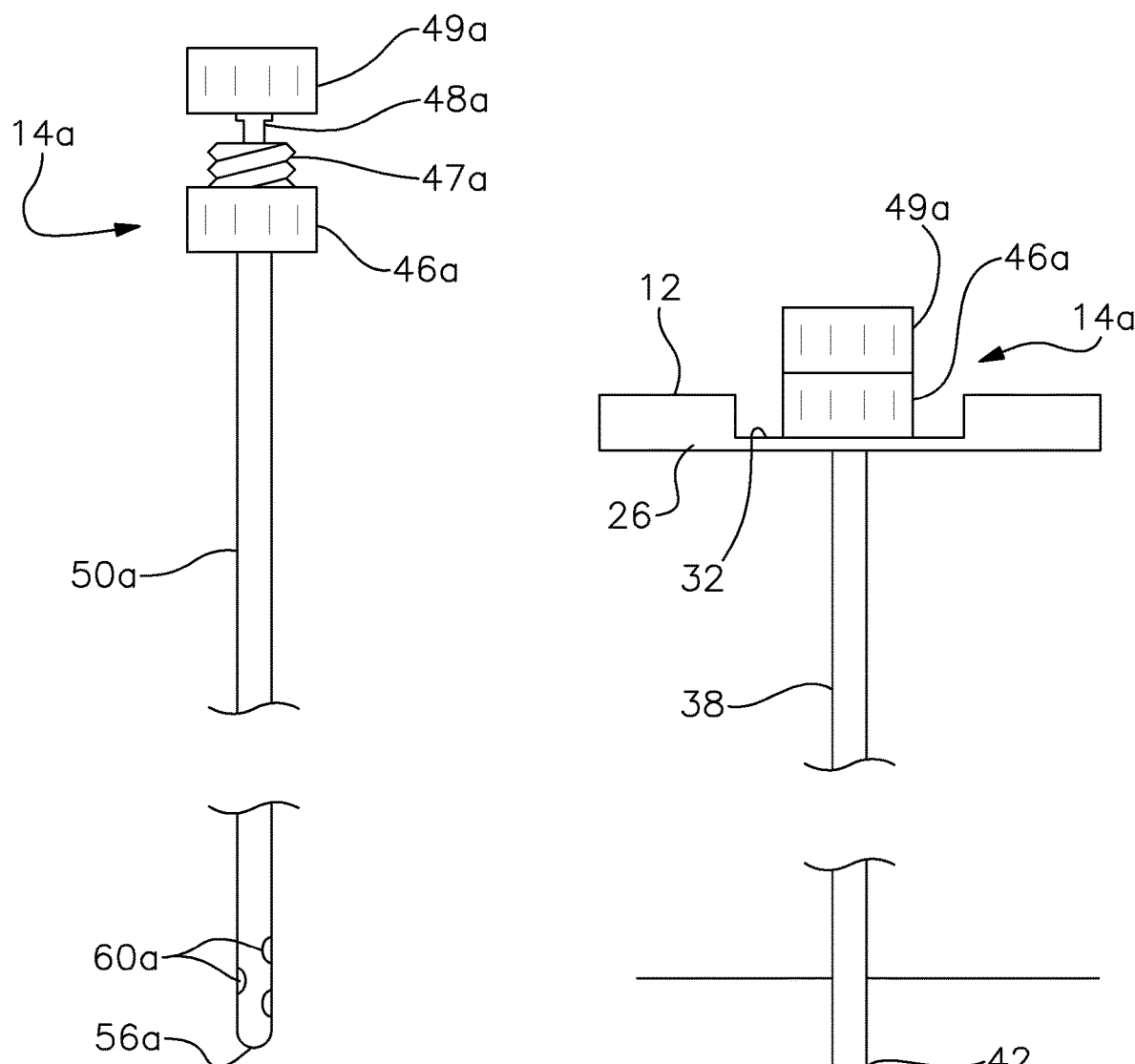
FIG. 8 is an elevational front end fragmentary view of an alternative harvesting cannula wherein the support hub supports an optional mallet cap.
Figure 9:
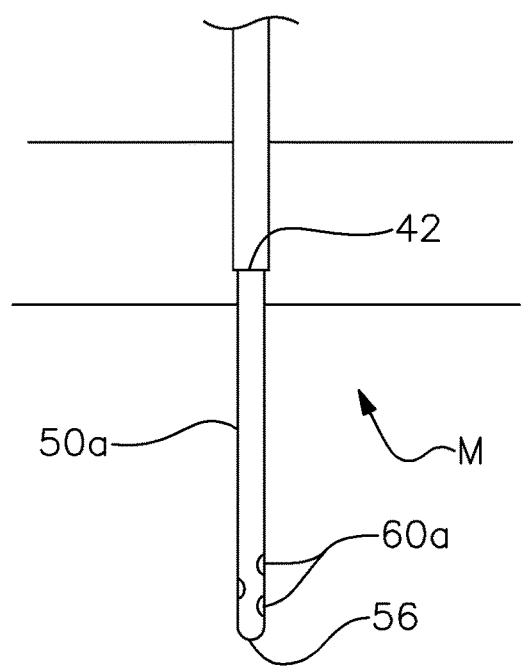
FIG. 9 is an elevational, fragmentary and partly cross sectional view of the harvesting component of FIG. 8 assembled within the introducer component and introduced into the bone marrow of the patient.

An alternative harvesting component 14a is shown in FIGS. 8 and 9. Harvesting component 14a includes a cylindrical support hub 46a that again carries an elongate depending harvesting cannula 50a. As in the prior embodiment, the harvesting cannula 50a includes a blunt distal tip 56a and aspiration openings 60a in the fenestrated side walls of cannula 50a above and proximate to blunt distal tip 56a.

Support hub 46a may enclose an annular locking element (not shown) of the type analogous to that previously described, which interengages a corresponding locking pin on the introducer component to secure the harvesting and introducer components together when they are assembled. Other forms of interlocking connections may be employed within the scope of this invention. In some versions the respective components may not be interlocked when they are interengaged or assembled.

Support hub 46a also supports an upper threaded extension 47a. An aspirating port 48a extends through threaded extension 47a and support hub 46a in communication with harvesting cannula 50a. A cylindrical mallet cap 49a is threadably attachable to threaded extension 48a such that when the mallet cap is attached to the harvesting component, cap 49a and support hub 46a join together as shown in FIG. 9.

In operation, the harvesting component 14a of FIGS. 8 and 9 is installed and operated analogously to the previously described harvesting component. Specifically, after the trocar component is removed, mallet cap 49a is attached to threaded extension 47a and the harvesting component is operably interengaged with introducer component 12. Specifically, harvesting cannula 50a is inserted through inlet 34 (see FIG. 2) and introducer cannula 38 to position blunt tip 60a slightly (about 1 cm) within the trabecular bone. Handle 26 of introducer component 12 is retracted to engage support hub 46a with the recess 22 of handle 12. The assembled introducer and harvesting components are then manipulated by the user to advance cannula 50a through bone marrow M. This advancement is facilitated by the interconnected support hub 46a and mallet cap 49a. See FIG. 9. As in the previously described embodiment, the lower end 42 of the introducer cannula remains in either the fat/tissue layer or in the cortical bone and is restrained from advancing into the trabecular bone and bone marrow M and causing undue damage therein. Only the blunt tip 60a and smooth sides of harvesting cannula 50a advance through the bone marrow to the depth and location selected for aspiration. When this location is reached, mallet cap 49a is detached from extension section 47a. An aspirating syringe is secured to aspiration port 40a and aspiration occurs as in the previously described version.

In all versions of this invention, significantly less damage is caused to the bone marrow sample and the blood cells of that sample. Specifically, by employing a smooth, rounded, blunt tip the harvesting cannula advances through the marrow without unduly damaging red blood cells and thereby releasing pre-hemoglobin molecules which are oxidative and destructive to tissue. The fenestrated sides of the present invention and relatively large openings achieve a gentle aspirating flow, as the harvesting cannula is gradually withdrawn from the marrow, which further reduces cell damage and improves the quality of the aspired sample. The small blunt tip and absence of a sharp cutting edge on the harvesting cannula allow the user to navigate the harvesting cannula effectively in various selected directions through the trabecular bone and bone marrow. The harvesting cannula advances through the bone marrow independently of the introducer cannula which remains outside of the marrow during collection of the sample. In the present invention, the sharp trocar edge is introduced at most only about 1 cm into the marrow. Thereafter, the blunt tip harvesting cannula can be advanced 3 cm or more into the marrow without causing anywhere near the degree of damage that would be caused by employing a sharp tip trocar or sharp edge cannula.

The system and method of this invention enables far less damage to be done to the trabecular bone, bone marrow and constituent cells during deployment of the aspiration instrumentation and collection of the aspirate sample. The system described herein is accompanied by greatly reduced tissue activation, free hemoglobin production and clotting. As a result, the system produces a significantly improved bone marrow aspirate sample, which can be processed effectively to achieve a bone marrow concentrate that is supraphysiologic in regenerative progenitor stem cells. The recovered stem cells may then be used effectively in a variety of medical treatments, therapies and other procedures.

From the foregoing it may be seen that the apparatus of this invention provides for a bone marrow aspirate collection system, which system for harvesting bone marrow aspirate yields an improved high quality concentration of regenerative progenitor stem cells for use in medical applications. The invention also pertains to a related method for using this system. While this detailed description has set forth particularly preferred embodiments of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

What is claimed is:

1. A bone marrow aspirate collection system comprising:
   a trocar component having an upper handle and an elongate shaft connected to and depending from said upper handle, the shaft terminating in a cutting edge at a lower end of said shaft;
   an introducer component including a lower handle and an introducer cannula connected to and depending from said lower handle, said introducer cannula including a sidewall and an open lower end, said sidewall having no openings, said introducer component further including an introducer inlet formed through said lower handle in communication with said introducer cannula, said trocar shaft being configured to be inserted longitudinally through said introducer inlet and said introducer cannula and said upper handle of said trocar and said lower handle of said introducer component being configured to be interengaged to selectively attach said trocar component to said introducer component and dispose said cutting edge of said trocar shaft beyond the open lower end of said introducer cannula; said upper and lower handles of said trocar component and said introducer component respectively being configured to be disengaged and said trocar shaft being configured to be withdrawn from said introducer cannula to selectively detach said trocar component from said introducer component; and
   a harvesting component that includes a support hub and a harvesting cannula carried by and depending from said support hub, said harvesting component further including an aspiration port communicably connected through said support hub to an upper end of said harvesting cannula, an opposite lower end of said harvesting cannula including a blunt tip, said harvesting cannula having one or more aspiration openings formed above said blunt tip and through a longitudinal side of said harvesting cannula;
   said harvesting cannula being configured to be inserted through said introducer inlet and said introducer cannula, and said support hub of said harvesting cannula being configured to be interengaged with said lower handle of said introducer cannula to selectively attach said harvesting component to said introducer component and dispose said blunt tip of said harvesting cannula beyond said open lower end of said introducing cannula;
   said support hub of said harvesting component and said lower handle of said introducer component being configured to be disengaged, and said harvesting cannula being configured to be withdrawn from said introducer cannula to selectively detach said harvesting component from said introducer component.

2. The system of claim 1 in which said trocar and harvesting components include respective connector sections, each said connector section including a respective first locking element, and said inlet of said introducer component including a complementary second locking element that is configured to be interengaged with a selected one of said first locking elements to releasably interlock a selected one of said trocar component and said harvesting component to said introducer component.

3. The system of claim 1 in which said introducer cannula and said harvesting cannula include respective depth markings formed at selected intervals along each said cannula.

4. The system of claim 1 in which said aspiration port of said harvesting component is for releasably and operably interconnecting to an aspirating syringe.

5. The system of claim 1 further including a mallet cap that is configured to be releasably attached to a top of said support hub.

6. A bone marrow aspirate collection system for penetrating the skin, underlying tissue and cortical bone of a patient and aspirating underlying bone marrow from the patient, said system comprising:
   a trocar component having an upper handle and an elongate shaft connected to and depending from said upper handle, the shaft terminating in a cutting edge at a lower end of said shaft;
   an introducer component including a lower handle and an introducer cannula connected to and depending from said lower handle, said introducer cannula including a sidewall and an open lower end, said sidewall having no openings, said introducer component further including an introducer inlet formed through said lower handle in communication with said introducer cannula, said trocar shaft being configured to be inserted longitudinally through said introducer inlet and said introducer cannula and said upper handle of said trocar component and said lower handle of said introducer component being configured to be interengaged to selectively attach said trocar component to said introducer component and dispose said cutting edge of said trocar shaft beyond said open lower end of said introducer cannula, said trocar and introducer components being configured to be manipulated when interengaged to insert said trocar shaft and said introducer cannula through the skin, underlying tissue and cortical bone of the patient until said cutting edge of said trocar shaft penetrates into the bone marrow of the patient, said upper and lower handles being configured to be disengaged and said trocar shaft being configured to be withdrawn from said introducer cannula to detach and remove said trocar shaft from said introducer component while said introducer cannula remains engaged with the patient; and
   a harvesting component including a support hub that carries an elongate harvesting cannula depending from said support hub and an aspiration port communicably connected through said support hub to an upper end of said harvesting cannula, an opposite lower end of said harvesting cannula including a blunt tip, said harvesting cannula including one or more aspiration openings formed above said blunt tip along a longitudinal side of said harvesting cannula; said harvesting cannula being configured to be inserted through said inlet of said introducer component and through said introducer cannula and said support hub of said harvesting component being configured to be interengaged with said lower handle of said introducer component to selectively attach said introducer component to said harvesting component and dispose said blunt tip of said harvesting cannula beyond said open lower end of said introducer cannula within the bone marrow of said patient; whereby said introducer cannula and harvesting cannula are configured to be manipulated when attached to position said harvesting cannula at a selected location within the patient's bone marrow for aspirating bone marrow through said harvesting cannula and said aspirating port.

7. The system of claim 6 further including an aspirating syringe configured to be connected to said aspirating port of said harvesting component said aspirating syringe being configured to be operated to aspirate a patient's bone marrow through said harvesting cannula and said harvesting aspirating port.

8. The system of claim 6 in which said trocar and harvesting components include respective connector sections, each said connector section including a respective first locking element, and said inlet of said introducer component including a complementary second locking element that is configured to be interengaged with a selected one of said first locking elements to releasably interlock a selected one of said trocar component and said harvesting component to said introducer component.

9. The system of claim 6 in which said introducer cannula and said harvesting cannula include respective depth markings formed at selected intervals along each said cannula.

10. The system of claim 6 in which said aspiration port of said harvesting component is configured to be releasably interconnected to an aspirating syringe.

11. The system of claim 6 in which said handle includes a mallet cap that is configured to be releasably attached to said support hub.

12. A method of collecting bone marrow aspirate from a patient, said method comprising:

providing a trocar component having an upper handle and an elongate trocar shaft connected to and depending from the upper handle, the shaft terminating in a cutting edge at a lower end of the shaft;

providing an introducer component that includes a lower handle and an introducer cannula, said introducer cannula including a sidewall and an open lower end, said sidewall having no openings, said introducer cannula connected to and depending from the lower handle and forming an introducer inlet through the lower handle in communication with the introducer cannula;

providing a harvesting component that includes a support hub carrying an elongate harvesting cannula depending from the support hub and having a blunt lower end and one or more aspiration openings formed above and proximate the blunt lower end along a longitudinal side of the harvesting cannula;

providing an aspiration port communicably connected through the support hub to an upper end of the harvesting cannula;

inserting the elongate trocar shaft component through the introducer inlet and introducer cannula to dispose the cutting edge of the trocar shaft beyond the open lower end of the introducer cannula;

interengaging the upper and lower handles and manipulating the trocar and introducer components to insert the introducer cannula and trocar shaft through the skin, underlying tissue and cortical bone of the patient until the cutting edge of the trocar shaft penetrates the bone marrow;

disengaging the upper and lower handles from one another and withdrawing the trocar component through the introducer cannula to detach the trocar component from the introducer component and disengage the trocar component from the patient while allowing the introducer component to remain engaged with the patient with the open lower end of the introducer cannula proximate the bone marrow of the patient;

interengaging the harvesting component with the introducer component by inserting the harvesting cannula through the introducer inlet and introducer cannula to position the blunt tip of the harvesting cannula beyond the open lower end of the introducer cannula and within the bone marrow of the patient;

interengaging the inlet port of the introducer component with the support hub of the harvesting component;

manipulating the harvesting component to position the harvesting cannula at a selected depth and location within the bone marrow; and aspirating bone marrow through the harvesting cannula and aspirating port of the harvesting component.

13. The method of claim 12 further including the step of releasably interlocking the trocar and introducer components when interengaged prior to inserting the introducer cannula and trocar shaft through the skin, underlying tissue and cortical bone of the patient.

14. The method of claim 13 further including the step of unlocking the trocar component from the introducer component and withdrawing the trocar shaft through the introducer cannula while the introducer cannula remains engaged with the patient.

15. The method of claim 12 further including the step of releasably interlocking the support hub of said harvesting component and said lower handle of the introducer component prior to manipulating the interengaged introducer component and harvesting component to position the harvesting cannula at a selected depth and location within the bone marrow.

16. The method of claim 15 further including the steps of withdrawing the introducer and harvesting components from the patient and unlocking the introducer and the harvesting components from one another after aspiration of the bone marrow through the harvesting cannula and aspiration port are completed.

17. A bone marrow aspirate collection system comprising:

a trocar component having an upper handle and an elongate shaft connected to and depending from said upper handle, the shaft terminating in a cutting edge at a lower end of said shaft;

an introducer component including a lower handle and an introducer cannula connected to and depending from said lower handle, said introducer cannula including an open lower end, said introducer component further including an introducer inlet formed through said lower handle in communication with said introducer cannula, said trocar shaft being configured to be inserted longitudinally through said introducer inlet and said introducer cannula and said upper handle of said trocar and said lower handle of said introducer component being configured to be interengaged to selectively attach said trocar component to said introducer component and dispose said cutting edge of said trocar shaft beyond the open lower end of said introducer cannula; said upper and lower handles of said trocar component and said introducer component respectively being configured to be disengaged and said trocar shaft being configured to be withdrawn from said introducer cannula to selectively detach said trocar component from said introducer component; and a harvesting component that includes a support hub and a harvesting cannula carried by and depending from said support hub, said harvesting component further including an aspiration port communicably connected through said support hub to an upper end of said harvesting cannula, an opposite lower end of said harvesting cannula including a blunt tip, said harvesting cannula having one or more aspiration openings formed above said blunt tip and through a longitudinal side of said harvesting cannula;

said harvesting cannula being configured to be inserted through said introducer inlet and said introducer cannula, and said support hub of said harvesting cannula being configured to be interengaged with said lower handle of said introducer cannula to selectively attach said harvesting component to said introducer component and dispose said blunt tip and said one or more aspiration openings of said harvesting cannula beyond said open lower end of said introducer cannula;

said support hub of said harvesting component and said lower handle of said introducer component being configured to be disengaged and said harvesting cannula being configured to be withdrawn from said introducer cannula to selectively detach said harvesting component from said introducer component.

18. A bone marrow aspirate collection system for penetrating the skin, underlying tissue and cortical bone of a patient and aspirating underlying bone marrow from the patient, said system comprising:

a trocar component having an upper handle and an elongate shaft connected to and depending from said upper handle, the shaft terminating in a cutting edge at a lower end of said shaft;

an introducer component including a lower handle and an introducer cannula connected to and depending from said lower handle, said introducer cannula including an open lower end, said introducer component further including an introducer inlet formed through said lower handle in communication with said introducer cannula, said trocar shaft being configured to be inserted longitudinally through said introducer inlet and said introducer cannula and said upper handle of said trocar component and said lower handle of said introducer component being configured to be interengaged to selectively attach said trocar component to said introducer component and dispose said cutting edge of said trocar shaft beyond said open lower end of said introducer cannula, said trocar and introducer components being configured to be manipulated when interengaged to insert said trocar shaft and said introducer cannula through the skin, underlying tissue and cortical bone of the patient until said cutting edge of said trocar shaft penetrates into the bone marrow of the patient, said upper and lower handles being configured to be disengaged and said trocar shaft being configured to be withdrawn from said introducer cannula to detach and remove said trocar shaft from said introducer component while said introducer cannula remains engaged with the patient; and a harvesting component including a support hub that carries an elongate harvesting cannula depending from said support hub and an aspiration port communicably connected through said support hub to an upper end of said harvesting cannula, an opposite lower end of said harvesting cannula including a blunt tip, said harvesting cannula including one or more aspiration openings formed above said blunt tip along a longitudinal side of said harvesting cannula; said harvesting cannula being configured to be inserted through said inlet of said introducer component and through said introducer cannula and said support hub of said harvesting component being configured to be interengaged with said lower handle of said introducer component to selectively attach said introducer component to said harvesting component and dispose said blunt tip and the one or more aspiration openings of said harvesting cannula beyond said open lower end of said introducer cannula within the bone marrow of said patient; whereby said introducer cannula and harvesting cannula are configured to be manipulated when attached to position said harvesting cannula at a selected location within the patient's bone marrow for aspirating bone marrow through said harvesting cannula and said aspirating port.

19. A method of collecting bone marrow aspirate from a patient, said method comprising:

providing a trocar component having an upper handle and an elongate trocar shaft connected to and depending from the upper handle, the shaft terminating in a cutting edge at a lower end of the shaft;

providing an introducer component that includes a lower handle and an introducer cannula, said introducer cannula including an open lower end, said introducer cannula connected to and depending from the lower handle and forming an introducer inlet through the lower handle in communication with the introducer cannula;

providing a harvesting component that includes a support hub carrying an elongate harvesting cannula depending from the support hub and having a blunt lower end and one or more aspiration openings formed above and proximate the blunt lower end along a longitudinal side of the harvesting cannula;

providing an aspiration port communicably connected through the support hub to an upper end of the harvesting cannula;

inserting the elongate trocar shaft component through the introducer inlet and introducer cannula to dispose the cutting edge of the trocar shaft beyond the open lower end of the introducer cannula;

interengaging the upper and lower handles and manipulating the trocar and introducer components to insert the introducer cannula and trocar shaft through the skin, underlying tissue and cortical bone of the patient until the cutting edge of the trocar shaft penetrates the bone marrow;

disengaging the upper and lower handles from one another and withdrawing the trocar component through the introducer cannula to detach the trocar component from the introducer component and disengage the trocar component from the patient while allowing the introducer component to remain engaged with the patient with the open lower end of the introducer cannula proximate the bone marrow of the patient;

interengaging the harvesting component with the introducer component by inserting the harvesting cannula through the introducer inlet and introducer cannula to position the blunt tip and the one or more aspiration openings of the harvesting cannula beyond the open lower end of the introducer cannula and within the bone marrow of the patient;
interengaging the inlet port of the introducer component with the support hub of the harvesting component;
manipulating the harvesting component to position the harvesting cannula at a selected depth and location within the bone marrow without advancing the lower end of the introducer cannula through the bone marrow; and
aspirating bone marrow through the harvesting cannula and aspirating port of the harvesting component.

* * * * *